| (12) | United States Patent | (10) Patent No.: | US 9,687,178 B2 |
|---|---|---|---|
| | Roxhed et al. | (45) Date of Patent: | Jun. 27, 2017 |

(54) MICROMACHINED FLUID FLOW REGULATING DEVICE

(71) Applicant: Niclas Roxhed, Bromma (SE)

(72) Inventors: Niclas Roxhed, Bromma (SE); Staffan Johansson, Bro (SE); Goran Stemme, Lidingo (SE); Hans Peter Starck Johnson, Stockholm (SE)

(73) Assignee: Niclas Roxhed, Bromma (SE)

( * ) Notice: Subject to any disclaimer, the term of this patent is extended or adjusted under 35 U.S.C. 154(b) by 577 days.

(21) Appl. No.: 14/157,810

(22) Filed: Jan. 17, 2014

(65) Prior Publication Data
US 2014/0207014 A1    Jul. 24, 2014

(30) Foreign Application Priority Data

Jan. 18, 2013 (SE) ...................... 1350059

(51) Int. Cl.
| *A61B 5/08* | (2006.01) |
| *A61B 5/087* | (2006.01) |
| *A61B 5/097* | (2006.01) |

(52) U.S. Cl.
CPC ............. *A61B 5/087* (2013.01); *A61B 5/082* (2013.01); *A61B 5/097* (2013.01); *A61B 2562/028* (2013.01); *A61B 2562/12* (2013.01)

(58) Field of Classification Search
None
See application file for complete search history.

(56) References Cited

U.S. PATENT DOCUMENTS

| 3,298,362 A | * | 1/1967 | Lippitt, Jr | A61B 5/087 |
| | | | | 482/13 |
| 3,699,296 A | | 10/1972 | Harris | |
| 6,238,352 B1 | * | 5/2001 | Gillings | A61B 5/087 |
| | | | | 600/529 |
| 2004/0082872 A1 | * | 4/2004 | von Bahr | A61B 5/0803 |
| | | | | 600/532 |

FOREIGN PATENT DOCUMENTS

WO    2006/080885 A1    8/2006

OTHER PUBLICATIONS

ATS/ERS Recommendations for Standardized Procedures for the Online and Offline Measurement of Exhaled Lower Respiratory Nitric Oxide and Nasal Nitric Oxide, 2005, Am J Respir Crit Care Med, vol. 171. pp. 912-930, 2005.

\* cited by examiner

*Primary Examiner* — Navin Natnithithadha
*Assistant Examiner* — Michael R Bloch
(74) *Attorney, Agent, or Firm* — Renner, Otto, Boisselle & Sklar, LLP

(57) ABSTRACT

A micromachined fluid flow regulating device is disclosed comprising a fluid flow channel, at least one flow orifice formed in the channel, defining an inlet portion of the channel upstream of the flow orifice, an outlet portion of the channel downstream of the flow orifice, the fluid having a flow direction from the inlet portion to the outlet portion of the channel. At least one piston is arranged upstream of the flow orifice, movably suspended in the channel by a spring means such that the piston is movable by the fluid in the flow direction of the fluid, towards the flow orifice, to regulate a fluid flow through the flow orifice. The disclosure further relates to the use of a micromachined flow regulating device in a breath analysis device and to a method of fabricating a flow regulating device.

31 Claims, 3 Drawing Sheets

MICROMACHINED FLUID FLOW REGULATING DEVICE

TECHNICAL FIELD

The present invention relates generally to a fluid flow regulating device, the use of such a fluid flow regulating device in a breath analysis device and a method of fabricating such a fluid flow regulating device

BACKGROUND ART

Exhaled breath diagnostics as a clinical method is reaching more and more acceptance in a variety of different diseases. To ensure reproducible measurement results, exhaled breath from patients should conform to certain protocols dictating the physical parameters (e.g. flow rate, pressure, temperature etc.) under which the test should be made. Thus it is sought to perform measurements under substantially constant flow of exhaled breath, despite variations in applied pressure.

In WO 2006/080885 A1 a constant flow regulator device for maintaining a constant flow of fluid is disclosed. The device comprises an inlet duct for incoming fluid, a housing, and a movable partition facing the inlet duct and being subjected to an elastic force. A fluid passage of variable cross section area is formed between the inlet duct and the movable partition. The housing and movable partition form an inner compartment in fluid communication with the inlet duct for establishing a fluid pressure inside the inner compartment approximately equal to the fluid pressure in the inlet duct. The size of the movable partition is significantly greater than the size of the inlet duct such that, in use, the partition is moved towards the inlet duct against the elastic force when the fluid pressure in the inlet duct increases to reduce said fluid passage cross section area, and vice versa, thereby maintaining constant fluid flow.

The current trend towards handheld point-of-care devices has brought a need for miniaturized flow handling systems. The previously disclosed device requires a significant size of the partition. It is therefore desired to find alternative solutions to the problem of regulating a fluid flow that may be suitable for miniaturisation, and that still may be used to regulate the relatively large flows of exhaled breath. For example, in asthma monitoring (fractional exhaled NO, FENO), regulatory guidelines dictates that measurements of nitric oxide concentration should be made at an exhaled flow rate of 50±5 ml/s (ATS/ERS recommendations for standardized procedures for the online and offline measurement of exhaled lower respiratory oxide and nasal nitric oxide, 2005. Am J Respir Crit Care Med 2005; 171:912-930).

SUMMARY OF INVENTION

An object of the present invention is to reduce the shortcomings of the above mentioned devices.

In particular it is an object of the present invention to provide a fluid flow regulating device which may be integrated in handheld analysis devices. It is further an object to provide a fluid flow regulating device which is able to passively regulate a comparatively large fluid flow in relation to its size. It is also sought to provide a fluid flow regulating device which may be produced at a reduced cost.

Thus the invention relates to a micromachined fluid flow regulating device comprising a fluid flow channel. At least one flow orifice is formed in the channel, defining an inlet portion of the channel upstream of the flow orifice and an outlet portion of the channel downstream of the flow orifice. The fluid has a flow direction defined from the inlet portion to the outlet portion of the channel. At least one piston is arranged upstream of the flow orifice, movably suspended in the channel by a spring means such that the piston is movable by the fluid, in the flow direction of the fluid, towards the flow orifice, to regulate a fluid flow through the flow orifice.

By providing a fluid flow regulating device with a fluid flow channel wherein at least one piston is movable, by the fluid, in the flow direction of the fluid towards at least one flow orifice, the device may be able to passively regulate a comparatively large fluid flow fluid flow in relation to its size. The construction allows for comparably large movements of the at least one piston in relation to the at least one orifice, further facilitating the regulation of a comparatively large fluid flow in relation to the size of the device.

By means of micromachining, a miniaturised flow regulating device which may be integrated in hand held analysis devices may be produced in a cost efficient manner. Further, the device may be manufactured with a high dimensional accuracy to provide a high precision in flow regulation of the fluid. This relates e.g. to the manufacturing of the at least one flow orifice, the at least one piston and the spring means.

In the device, the flow may be regulated to be contained within a certain flow interval, over a certain range of applied pressure of the applied fluid. The flow may be regulated at a comparatively large fluid flow in relation to the size of the device, such as within a range of 50±5 ml/s. The device may be configured to provide the sought flow within the range of 50±5 ml/s over a pressure in the range of 1-2 kPa applied over the device. The fluid may be a gas, such as exhaled breath from a person whose breath is to be analysed.

The fluid flow channel may be a planar fluid flow channel, and the piston may be movable in the plane of the channel. Thus the fabrication of the device may be simplified.

The inlet portion of the channel, the at least one flow orifice and the outlet portion may be arranged in line with each other, or in the plane of the channel. Thus unwanted pressure drop over the device may be reduced.

The micromachined fluid flow regulating device may comprise a plurality of flow orifices and a plurality of pistons. Thus the at least one flow orifice and at least one piston may be a plurality of flow orifices and a plurality of pistons. This may be beneficial in a miniaturised microfabricated device, due to scaling effects when decreasing the dimensions of the features. The number of flow orifices may be in the range of 4-20, preferably in the range of 5-10, more preferably 6.

The flow of fluid through each flow orifice of the plurality of flow orifices may be regulated by a corresponding piston of the plurality of pistons, arranged upstream of respective flow orifice. Thus the flow through each flow orifice may be controlled individually or jointly. Each piston may be miniaturised to a size corresponding to the size of respective flow orifice thus allowing an overall compact design.

The plurality of flow orifices may be arranged as a linear array of flow orifices across the fluid flow channel. Each flow orifice may be formed between two stationary flow restriction posts extending into the fluid channel spaced apart from one another. Thus the construction may be compact and suitable for planar fabrication.

The stationary flow restriction posts may have a shape along the direction of fluid flow provided with an acute trailing edge. Thus the formation of turbulence or wakes in the device may be reduced, limiting the pressure drop over the device.

Each stationary flow restriction post and the corresponding piston may define a passage between one another, which passage has a cross-sectional extension which is dependent on the position of the piston relative to the stationary flow restriction post, whereby the flow through the passage may be regulated by moving the piston towards the flow orifice formed by the stationary flow restriction posts. The stationary flow restriction posts and/or the piston may be formed such that the passage varies in a linear or non-linear way while moving the piston towards the flow orifice formed by the stationary flow restriction posts. Thus the flow-pressure relationship of the device may be tailored over specific ranges of applied pressure.

The flow regulating device may be configured such that the pistons are moved by fluid forces only during operation of the device. Thus the fluid flow and/or the differential pressure itself regulates the flow resistance through the device, without the need for active flow regulation. The flow regulating device may be configured such that the pistons are moved by the differential pressure over the inlet portion and the outlet portion during operation of the device.

Each piston may have a rectangular shape along the flow direction. Alternatively the pistons may have a shape to increase the area facing the inlet portion of the channel, such as a T-shape.

The plurality of pistons may be configured to be movable as a unit, and the spring means may be configured to suspend the unit of the plurality of pistons. Thus the construction of the device may be simplified and the operation of the device more reliable due to a smaller number of moving parts. The plurality of pistons may be connected by at least one beam to form a unit.

The plurality of pistons may be suspended in the channel such that to provide a linear movement of the plurality of pistons towards the flow orifices along the direction of fluid flow, preferably wherein the plurality of pistons may be suspended by two identical beam and spring structures to provide the linear movement. Thus the formation of a unit suspended in the channel may be achieved.

The spring means may comprise a plurality of springs, preferably formed in monocrystalline silicon. Each spring may be formed as a U-shaped beam. Silicon is preferred due to its excellent material properties, allowing for repeated large deflections of the springs with minimal fatigue. The U-shaped springs allows for large deflections of a compact spring.

The spring means may comprises a non-linear spring element, preferably a strain-loosening spring element such as such as a beam compressed in the length direction of the beam, to provide a non-linear displacement of the plurality of pistons when subjected to an increasing fluid flow and/or pressure drop.

The device may comprise a limiting arrangement to limit the movement of each piston towards the corresponding orifice and thus define a minimum flow passage through the orifice. The limiting arrangement may comprise a limiting post arranged in each orifice. Thus the device always allows for at least a minimum flow to pass through the device. The limiting arrangement also reduces the risk of damaging the spring means by limiting the deflection.

The fluid channel may have a width dimension in the plane of the channel which is larger or much larger than a height dimension of the channel, out of the plane of the channel. The flow orifices and the pistons may have a height dimension comparable to a height dimension of the fluid channel. Thus the full channel height is used. Alternatively the stationary posts and the pistons may have a height which is smaller than the height of the channel. This may allow the flow rate through the device to be higher.

The micromachined fluid flow regulating device may be configured to reach a full stroke of the pistons at an applied differential pressure in the range of 1-3 kPa, preferably 2 kPa, over the inlet and outlet portion of the fluid channel. Thus the device is suitable for regulating exhaled breath from a person.

The fluid flow channel may have a height dimension in the range of 10-1000 μm, preferably in the range of 100-600 μm and/or wherein the fluid flow channel may have a width dimension in the range of 100-10000 μm, preferably in the range of 1000-5000 μm, and/or wherein the flow orifices may have a width dimension in the range of 100-400 μm, preferably about 220 μm, and/or wherein the pistons may have a width dimension in the range of 100-400 μm, preferably about 220 μm, and/or wherein the device may be configured such that the pistons are movable towards the flow orifices over a range of 100-400 μm, preferably about 200 μm. The flow regulating device may have length, width and height dimensions in the range of 0.5-5 mm, preferably of about 2×4×2 mm (length×width×height).

The flow regulating device may be formed, at least in part, by micromachining. The flow regulating device may preferably be formed, at least in part, by micromachining in silicon. Silicon is preferred due to its ability to be machined at a high precision, and due to its mechanical properties. The mechanical properties of silicon allow an element such as the spring means to be subjected to alternating repetition of stress with a very low level of fatigue. Micromachining is defined to include fabrication techniques with a level of accuracy in the range below 10 μm, preferably in the range below 1 μm. Micromachining may include one or more of lithography, wet etching, dry etching (such as deep reactive ion etching, DRIE) etc, but may further include one or more of electron or ion bean machining, plasma beam machining, laser machining, electro discharge machining, micromilling, micromolding, microreplication in a polymer, micro solid freeform fabrication, micro stereo lithography, electroplating and the like. Micromachining allows for a miniaturised device that may be batch fabricated and thus produced at a reduced cost.

The flow regulating device may be formed by;
  providing a SOI (Silicon on insulator) wafer having a top silicon layer, an intermediate insulator layer and a bottom silicon layer,
  etching the spring means in the top silicon layer,
  providing a silicon wafer,
  etching a recess in the silicon wafer such that to provide a space for movability of the springs,
  bonding the silicon wafer and the SOI wafer with the recess in the silicon wafer facing the spring means,
  etching the channel, the plurality of pistons and a plurality of posts forming the plurality of flow orifices, in the bottom silicon layer,
  etching the insulator layer such that to release the pistons and spring means,
  providing a lid wafer, preferably a glass wafer,
  forming a recess in the lid wafer,
  bonding the lid wafer to the bottom silicon layer with the recess in the lid wafer facing the bottom silicon layer, and
  preferably dicing the bonded wafer structure into a plurality of devices.

The invention further relates to a breath analysis device comprising a flow regulating device as disclosed for regulating a flow of exhaled breath to maintain a flow in the range of 10-300 ml/s, preferably maintaining a flow of 50±5 ml/s. The breath analysis device may comprise a sensor 502 for analysing nitric oxide, NO, content in exhaled breath. For example, FIG. 4 shows an inlet/mouthpiece depicted as a leftmost rectangle, a flow regulating device 501 and a sensor 502. Thus the breath analysis device may be made compact and suitable for hand-held use or other point-of-care applications.

The invention further relates to a use of a flow regulating device as disclosed in a breath analysis device for regulating a flow of exhaled breath to maintain a flow in the range of 10-300 ml/s, preferably maintaining a flow of 50±5 ml/s during sample acquisition. Thus the analysis performed by the device may fulfil regulation guidelines.

The invention further relates to a method of fabricating a flow regulating device as disclosed. The method may comprise any of the steps of;

providing a SOI (Silicon on insulator) wafer having a top silicon layer, an intermediate insulator layer and a bottom silicon layer, etching the spring means in the top silicon layer, providing a silicon wafer, etching a recess in the silicon wafer such that to provide a space for movability of the springs, bonding the silicon wafer and the SOI wafer with the recess in the silicon wafer facing the spring means, etching the channel, the plurality of pistons and a plurality of posts forming the plurality of flow orifices, in the bottom silicon layer, etching the insulator layer such that to release the pistons and spring means, providing a lid wafer, preferably a glass wafer, forming a recess in the lid wafer, bonding the lid wafer to the bottom silicon layer with the recess in the lid wafer facing the bottom silicon layer, and/or preferably dicing the bonded wafer structure into a plurality of devices.

As used herein, the singular forms "a", "an" and "the" are intended to include plural forms as well, unless the context clearly indicates otherwise. The term about is defined to describe variations in the range of ±10%.

BRIEF DESCRIPTION OF DRAWINGS

The invention is now described, by way of example, with reference to the accompanying drawings, in which.

DESCRIPTION OF EMBODIMENTS

In the following, a detailed description of embodiments of the micromachined fluid flow regulating device is described with reference to the drawings.

Figure 1:
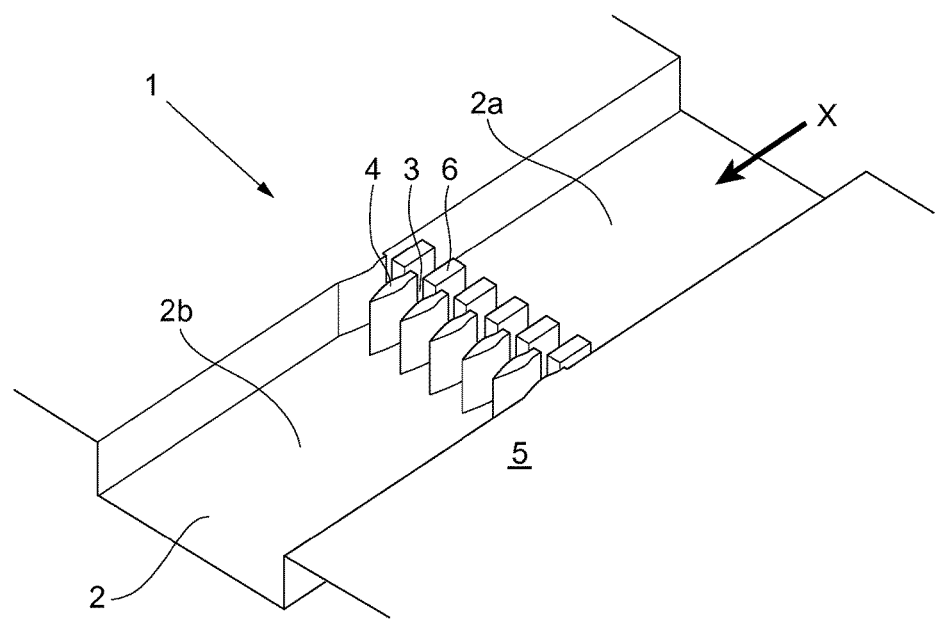
FIG. 1 shows a perspective view of a micromachined fluid flow regulating device.
Figure 2:
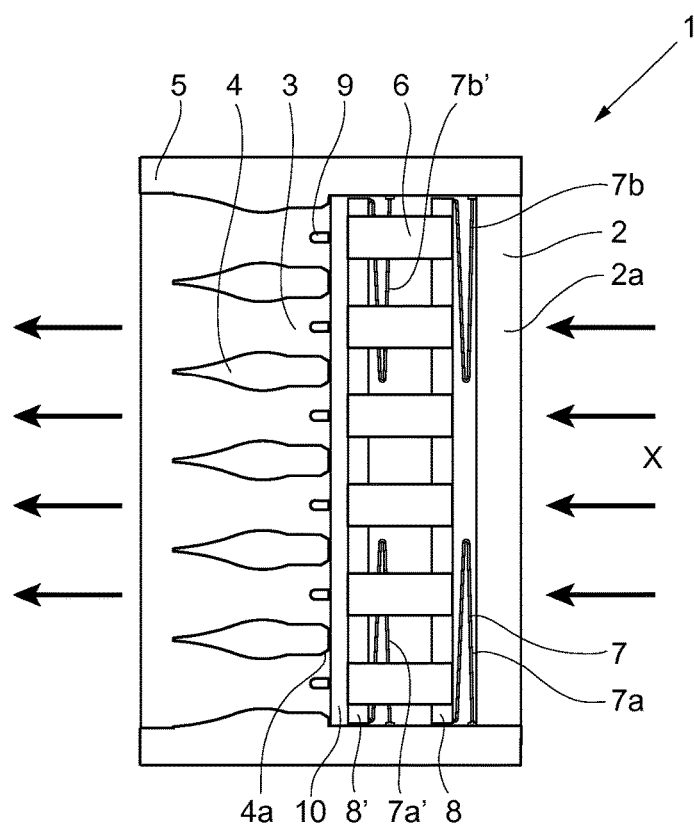
FIG. 2 shows a planar view of a micromachined fluid flow regulating device.

In FIG. 1 and FIG. 2, a miniaturised micromachined fluid flow regulating device 1 is shown wherein a planar fluid flow channel 2 is formed in a single crystalline silicon body 5. The flow channel is formed in a surface plane of a planar Silicon-on-Insulator (SOI) wafer being the starting material for fabricating the device, and from which the body 5 thereafter is cut. The fabrication of the micromachined fluid flow regulating device is described further below. In the channel, a flow of fluid, such as in the form of gas, will be received during operation, having a flow direction x defined as from an inlet portion 2a of the channel to an outlet portion 2b of the channel. The flow direction x is shown by arrows. The channel has a width of 2.8 mm (2800 μm), the width being defined in the plane of the channel and in a direction perpendicular to the flow direction x. In the direction of the width of the channel, the channel is delimited by channel walls. The channel has a height of 830 μm, the height being defined in a direction perpendicular to the flow direction x, and perpendicular to the plane of the channel. In the direction of height of the channel, the channel is delimited by a channel bottom end and a channel top end, the bottom end being defined as being positioned away from an upper planar surface of the silicon wafer being the starting material for fabricating the device. The channel top end is formed by a lid, such as a glass lid, enclosing the channel in the height direction.

In the channel, a plurality of flow orifices 3 is formed by a plurality of stationary flow restriction posts 4 extending into and bridging over the fluid channel in the height direction. In the example shown the device is provided with six flow orifices. The flow orifices define the inlet portion 2a of the channel upstream of the flow orifices and the outlet portion 2b of the channel downstream of the flow orifices. The stationary flow restriction posts are distributed as a linear array, forming a linear array of identical or similar flow orifices. The dimensions of the flow restriction posts in the plane of the channel are about 820×170 μm$^2$ (length× width).

Upstream of the flow orifices a plurality of pistons 6 is arranged. The number of pistons corresponds to the number of flow orifices. In the example shown the device is provided with six pistons. Each piston is provided with a rectangular shape in the plane of the channel, elongated in the direction of the flow of the fluid. The pistons are movably suspended in the body forming the channel by a spring means 7 in the form of two identical beam and spring structures such that the pistons are movable in parallel, towards the flow orifices to regulate a fluid flow through the flow orifices. Thus each piston is movable by the fluid in the flow direction x corresponding to a direction along a line extending between the inlet portion of the channel, one of the flow orifices, and the outlet portion of the channel. The dimensions of the pistons in the plane of the channel are about 520×220 μm$^2$.

The two beams 8 and 8' of the spring and beam structures connect the plurality of pistons to a unit. Each beam is attached to the body of the channel by two folded springs 7a, 7b, 7a', 7b'. The beams may be arranged in a recess 10 formed in the wall of the channel at the channel bottom end. Thus the influence on the flow of fluid in the channel by the beam and spring structure is diminished. The springs extend in a direction perpendicular to the direction of flow in the channel, and thus to the direction of movement of the pistons. Each spring is formed as an extended loop of single crystalline silicon, extending from a portion of the body close to each wall of the fluid channel. A first end of each spring is connected to a portion of the wall and a second end of each spring is connected to a portion of a beam. Each spring is formed as a folded U-shaped beam provided with a bend at a portion in-between the first and second end of the spring, and directed towards the middle of the channel. Each spring is about 11 μm wide with a loop length of 870 μm.

The thickness of each spring is about 20 µm, corresponding to the thickness of the device layer of the SOI wafer. The spring force of each spring is about 3 N/m, or 3.3 N/m. The spring means is configured such that the plurality of pistons is movable over a length of 200 µm in the direction of the flow. Due to the configuration of the spring and beam structures, a linear movement of the plurality of pistons towards the flow orifices along the direction of fluid flow is provided.

In an alternative embodiment, not shown, the spring means comprises at least one non-linear or strain-loosening spring element, such as a beam compressed in the length direction of the beam or a buckling spring mechanism (see e.g. U.S. Pat. No. 3,699,296). This element may provide a non-linear displacement of the pistons when subjected to an increasing differential pressure over the device during operation of the device.

In each flow orifice, i.e. in-between each flow restriction posts, and between the outermost flow restriction posts and the wall of the channel, a limiting post 9 is arranged. The dimensions of each limiting post in the plane of the channel are about 100×55 µm². The limiting posts are arranged such that the movement of the plurality of pistons towards the plurality of orifices is limited by the limiting posts, thus defining a minimum flow passage through the flow orifices. As an alternative, a limiting member may be arranged to limit the movement by the unit of pistons and beams by creating a stop for one of the beam, such as in contact with the flow restriction posts 4, a projection of the channel wall 5, or an end portion of the recess.

The shape of the flow restriction post is configured to provide the sought flow-pressure relationship. The stationary flow restriction posts and/or the piston may be formed such that the passage between the stationary flow restriction posts and the corresponding piston varies in a linear or non-linear way while moving the piston towards the flow orifice formed by the stationary flow restriction posts. In FIG. 2, the portion 4a of the stationary flow restriction posts facing the pistons is wedge shaped to tailor the flow resistance over the passage as dependent on the relative position of the piston to the stationary flow restriction post. In a similar way, the portion of the piston facing the stationary flow restriction post may be shaped to tailor the flow resistance over the passage as dependent on the relative position of the piston to the stationary flow restriction post. The portions of the pistons or stationary flow restriction post defining the passage may thus be rectangular, partially wedge shaped, rounded or provided with any other shape to tailor the pressure-flow behaviour of the device. Each flow restriction post may further be provided with a shape along the direction of fluid flow provided with a trailing edge having an acute angle to minimise flow disturbance.

Figure 3:
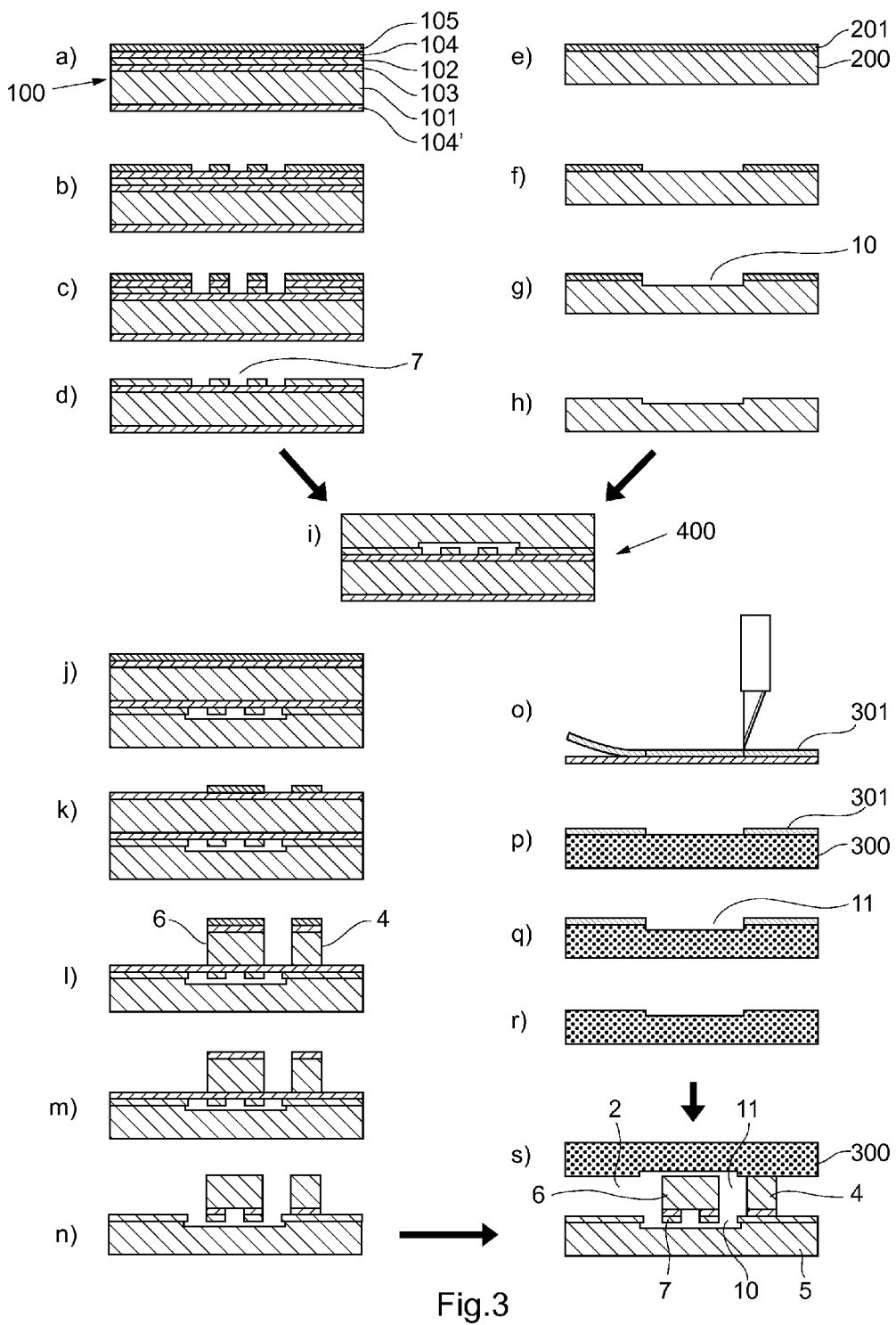
FIG. 3 shows an overview of fabrication steps in a method of fabricating a flow regulating device, showing cross-sectional views of the work piece at each such fabrication step.
Figure 4:
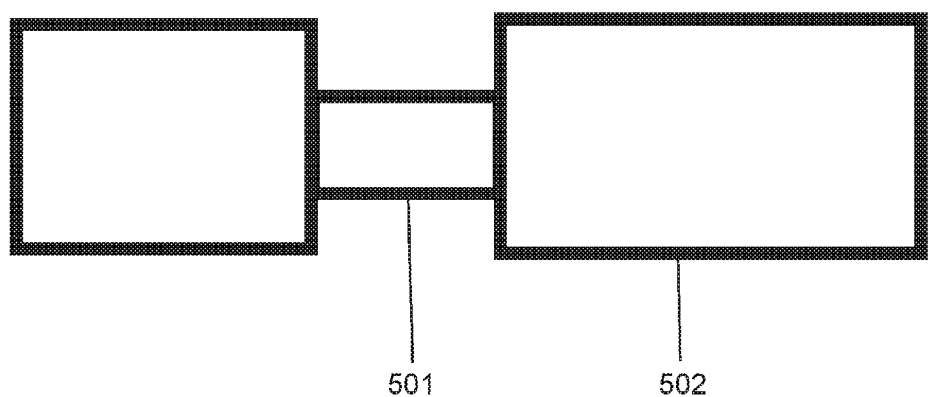
FIG. 4 shows a schematic view of the breath analysis device including a sensor.

With reference to FIG. 3, the fabrication of a miniaturised fluid flow regulating device is shown. A plurality of miniaturised micromachined fluid flow regulating devices may be batch fabricated by a repeated lithography and etching process. The starting material may be a silicon-on-insulator (SOI) wafer 100, a silicon wafer 200, and a borosilicate glass wafer 300 (borofloat). The wafers may be 100 mm diameter wafers. The SOI wafer comprises a first layer 101 (called handle layer) of single crystalline silicon such as having a thickness of 830 µm and a second layer 102 (called device layer) of single crystalline silicon such as having a thickness of 20 µm. Inbetween the two layers of silicon, an insulating layer 103 of silicon oxide is provided (buried oxide layer, box). The silicon-on-insulator (SOI) wafer may first be subjected to a step of wet thermal oxidation to obtain a silicon oxide layer 104, 104', preferably of about 3.5 µm oxide thickness at 1100° C. The SOI wafer may then be spin coated (FIG. 3a) to obtain a layer of photo resist 105 (e.g. Shipley 700-1.2 at 4000 rpm). Thereafter the layer of photo resist may be patterned by lithography (FIG. 3b). The oxide and device layer may thereafter be etched in two steps to fabricate the springs 7 (FIG. 3c); the oxide being etched by reactive ion etching (RIE, Applied Materials, P5000) while the silicon being etched by deep RIE (DRIE, STS ICP Multiplex ASE). The deep RIE may be performed at 600 W coil power and 12 W low-frequency platen power with 130 sccm Sulfur hexafluoride, SF6, flow for 6 minutes until the 1 µm thick buried oxide (box) layer was reached. The photo resist mask layer may then be removed by ashing in a O₂-plasma (TePla Model 300) (FIG. 3d). Thus the spring means 7 are formed.

To fabricate a bottom device cover with a recess 10 to enable piston and spring movement, a conventional double side polished silicon wafer (DSP) 200 may be processed. The wafer (such as 525 µm thick) may be processed (see FIG. 3 e-h) in a similar way as the SOI wafer excluding the oxide etch step shown in FIG. 3 c. The wafer may be spin coated (FIG. 3e) to obtain a layer of photo resist 201 (such as Shipley 700-1.2 at 4000 rpm). Thereafter the layer of photo resist may be patterned by lithography (FIG. 3f). The silicon may thereafter be etched by DRIE to fabricate the recess 10 (FIG. 3g). The recess may be about 30 µm deep, and the etch time about 10 minutes. The resist layer is thereafter removed, FIG. 3h.

The DSP wafer and the SOI wafer may then be fusion bonded to a wafer stack 400 (FIG. 3i) in a substrate bonder (Suss Microtec CB8), thus forming a unit. The bonding may be performed in vacuum at room temperature with 1 kN force for 1 minute. The bonding may be followed by annealing and wet thermal oxidation at 1000° C. to protect the springs by an oxide layer, such as 200 nm thick.

The bonded wafer stack 400 may then be processed by spinning a layer of photo resist (AZ9260, 2400 rpm) (FIG. 3j) to achieve approximately 10 µm photoresist thickness which may be patterned by UV-litography (1500 mJ/cm2) and developed (AZ 400K 1:4, 3 min) (FIG. 3k). The oxide may then be etched as described above, and the silicon may be etched using DRIE (FIG. 3l). The etching of the silicon may be performed as two steps. First, the wafer stack is etched with 600 W coil power and 11 W high-frequency platen power with 130 sccm SF6 flow for 3 hours until there is approximately 150 µm of silicon left before reaching the box layer. Then, the platen power may be switched to 12 W low-frequency whereby the etching continues to stop on the box layer after approximately 2 hours. The etching process finalizes the 830 µm high pistons 6 and posts 4 and the channel 2 itself. The channel height thus corresponds to the thickness of the handle layer of the SOI wafer. The photo resist may subsequently be removed by O₂-plasma ashing (FIG. 3m).

A top cover of the device may be fabricated from a glass wafer 200, such as 500 µm thick. A Nitto Denko dicing tape may be cut to form a mask 301 (FIG. 3o) which is transferred to the glass wafer (FIG. 3p). The dicing tape may be cut on a plastic liner foil using a Graphtec CE5000-60 cutting plotter and subsequently transferred to the glass by peeling it off from the liner and taping it to the glass wafer. To be able to easily detach the tape without distorting the pattern, an additional layer of the dicing tape may be used between the liner and the cut dicing tape. After transferring the mask to the wafer, a recess 11 may be formed in the wafer by sand blasting (FIG. 3*q*) to about 30 μm depth. The mask may thereafter be removed (FIG. 3*r*)

The fabrication of the flow regulator may thereafter be completed by anodic bonding of the glass wafer 300 onto the silicon wafer stack 400 (FIG. 3*s*), such that in a substrate bonder (Suss Microtec, CB8) at 1 kN force and 500 volts until the current dropped 10%.

The piston and spring structure 6, 7 may be released from the oxide (FIG. 3*n*) by etching in buffered hydrogen fluoride (BHF) for 100 minutes. Thus the pistons are movable suspended by the spring means 7 in a recess 10 formed in the bottom wall of the channel 2 and a recess 11 formed in the top wall of the channel.

As a final step the bonded stack of wafers may be diced in a dicing saw into a plurality of separate fluid flow regulating devices, each having a size of 2×2×4 mm³ (length×height×width).

The performance of the device may be adapted to various parameters of the fluid flow, such as flow and pressure ranges, by adjusting the height and width of the channel, the number, dimensions and geometry of the flow orifices etc. In particular the planar fabrication technique disclosed above allows the height of the channel to be chosen by selecting the thickness of the silicon-on-insulator (SOI) wafer handle layer. The spring constant of the springs may be chosen by selecting the thickness of the SOI device layer. Thus the performance of the device may be changed while maintaining the same set of masks for lithography.

During operation of the device a flow of fluid, such as exhaled breath from a person, is supplied through the channel 2, from the inlet portion 2*a* of the channel towards the outlet portion 2*b* of the channel. The fluid passes the plurality of pistons 6 and exerts a force on the plurality of pistons. Due to the drag force of the fluid flow and/or the pressure drop over the device, the unit of the plurality of pistons and the beams connecting the pistons with the springs are displaced in the direction x towards the plurality of flow orifices 3. Each of the plurality of pistons is thus displaced towards the respective flow orifice whereby the flow of fluid through each orifice is regulated by the displacement of the piston. The displacement of the unit of pistons is against the spring force of the spring means 7 comprising the set of springs 7*a*, 7*b*, 7*a*', 7*b*' suspending the unit of the plurality of pistons and the beams in the channel. The flow regulating function of the device is passive in the sense that the flow regulating device is configured such that the pistons are moved by a drag force of the fluid flow and/or the pressure drop over the device only during operation of the device.

What is claimed is:

1. A micromachined fluid flow regulating device for a fluid comprising:
   a fluid flow channel,
   at least one flow orifice formed in the fluid flow channel, defining an inlet portion of the fluid flow channel upstream of the at least one flow orifice, an outlet portion of the fluid flow channel downstream of the at least one flow orifice, the fluid when located in the fluid flow channel having a flow direction from the inlet portion to the outlet portion of the fluid flow channel,
   a spring,
   at least one piston arranged upstream of the at least one flow orifice, movably suspended in the channel by the spring such that the at least one piston is movable by the fluid in the flow direction of the fluid, towards the at least one flow orifice, to regulate a fluid flow through the at least one flow orifice,
   wherein the at least one flow orifice comprises a plurality of flow orifices and the at least one piston comprises a plurality of pistons.

2. The micromachined fluid flow regulating device according to claim 1 wherein the fluid flow channel is a planar fluid flow channel, and the at least one piston is movable in a plane of the planar fluid flow channel, towards the at least one flow orifice, to regulate a fluid flow through the at least one flow orifice.

3. The micromachined fluid flow regulating device according to claim 1, wherein a flow of the fluid through each flow orifice of the plurality of flow orifices is regulated by a corresponding piston of the plurality of pistons, arranged upstream of a respective flow orifice.

4. The micromachined fluid flow regulating device according to claim 1, wherein the plurality of flow orifices is arranged as a linear array of flow orifices across the fluid flow channel.

5. The micromachined fluid flow regulating device according to claim 1 wherein the micromachined fluid flow regulating device is configured such that the plurality of pistons are moved by fluid forces only during operation of the micromachined fluid flow device.

6. The micromachined fluid flow regulating device according to claim 5 wherein the micromachined fluid flow regulating device is configured such that the plurality of pistons are moved by differential pressure over the inlet portion and the outlet portion during operation of the micromachined fluid flow regulating device.

7. The micromachined fluid flow regulating device according to claim 1 wherein each of the at least one piston has a rectangular shape along the flow direction.

8. The micromachined fluid flow regulating device according to claim 1 wherein the plurality of pistons is configured to be movable as a unit, and the spring is configured to suspend the unit of the plurality of pistons.

9. The micromachined fluid flow regulating device according to claim 8 wherein the plurality of pistons is suspended in the fluid flow channel to provide a linear movement of the plurality of pistons towards the plurality of flow orifices along the direction of fluid flow.

10. The micromachined fluid flow regulating device according to claim 9 wherein the plurality of pistons are suspended by a plurality of beam and spring structures to provide the linear movement.

11. The micromachined fluid flow regulating device according to claim 1 wherein the spring comprises a plurality of springs.

12. The micromachined fluid flow regulating device according to claim 11 wherein each spring of the plurality of springs is formed as a U-shaped beam.

13. The micromachined fluid flow regulating device according to claim 1 wherein the spring comprises a non-linear spring element.

14. The micromachined fluid flow regulating device according to claim 1 wherein the micromachined fluid flow regulating device comprises a limiting arrangement to limit movement of the at least one piston towards a corresponding at least one flow orifice and thus define a minimum flow passage through the at least one flow orifice.

15. The micromachined fluid flow regulating device according to claim 14, wherein the limiting arrangement comprises a limiting post arranged in the at least one flow orifice.

16. The micromachined fluid flow regulating device according to claim 1 wherein the fluid flow channel has a width dimension in a plane of the channel that is larger than a height dimension of the channel, wherein the height dimension is out of the plane of the fluid flow channel.

17. The micromachined fluid flow regulating device according to claim 1 wherein the plurality of flow orifices is a number of flow orifices is in a range of 4-20.

18. The micromachined fluid flow regulating device according to claim 17 wherein the number of flow orifices is in the range of 5-10.

19. The micromachined fluid flow regulating device according to claim 18 wherein the number of flow orifices is 6.

20. The micromachined fluid flow regulating device according to claim 1 configured to reach a full stroke of the at least one piston at an applied differential pressure in a range of 1-3 kPa.

21. The micromachined fluid flow regulating device according to claim 1 wherein each of the at least one flow orifice and each of the at least one piston has a height dimension equal to a height dimension of the fluid flow channel.

22. The micromachined fluid flow regulating device according to claim 1 wherein the fluid flow channel has a height dimension in a range of 10-2000 μm, and/or wherein the fluid flow channel has a width dimension in the range of 100-10000 μm, and/or wherein each of the at least one flow orifice has a width dimension in the range of 50-400 μm, and/or wherein each of the at least one piston has a width dimension in the range of 100-400 μm, and/or wherein the micromachined fluid flow regulating device is configured such that each of the at least one piston is movable towards a corresponding at least one flow orifice over a range of 100-400 μm.

23. The micromachined flow regulating device according to claim 1 formed at least in part by micromachining in silicon.

24. The micromachined flow regulating device according to claim 1 formed by;
providing a silicon on insulator (SOI) wafer having a top silicon layer, an intermediate insulator layer and a bottom silicon layer,
etching the spring in the top silicon layer,
etching the fluid flow channel, the plurality of pistons and a plurality of posts forming the plurality of flow orifices, in the bottom silicon layer, and
etching the insulator layer to release the plurality of pistons and spring.

25. A breath analysis device comprising the micromachined flow regulating device according to claim 1 for regulating a flow of exhaled breath to maintain a flow in a range of 10-300 ml/s.

26. The breath analysis device according to claim 25 comprising a sensor for analysing nitric oxide (NO) content in exhaled breath.

27. A method of fabricating the flow regulating device according to claim 1, comprising;
providing a silicon on insulator (SOI) wafer having a top silicon layer, an intermediate insulator layer and a bottom silicon layer,
etching the spring in the top silicon layer,
etching the fluid flow channel, the plurality of pistons and a plurality of posts forming the plurality of flow orifices, in the bottom silicon layer, and
etching the insulator layer to release the plurality of pistons and spring.

28. The method according to claim 27 further comprising;
providing a silicon wafer,
etching a recess in the silicon wafer to provide a space for movability of the spring,
bonding the silicon wafer and the SOI wafer with the recess in the silicon wafer facing the spring.

29. The method according to claim 27 further comprising;
providing a lid wafer,
forming a recess in the lid wafer,
bonding the lid wafer to the bottom silicon layer with the recess in the lid wafer facing the bottom silicon layer.

30. A micromachined fluid flow regulating device for a fluid comprising:
a fluid flow channel,
at least one flow orifice formed in the fluid flow channel, defining an inlet portion of the fluid flow channel upstream of the at least one flow orifice, an outlet portion of the fluid flow channel downstream of the at least one flow orifice, the fluid when located in the fluid flow channel having a flow direction from the inlet portion to the outlet portion of the fluid flow channel,
a spring,
at least one piston arranged upstream of the at least one flow orifice, movably suspended in the fluid flow channel by the spring such that the at least one piston is movable by the fluid in the flow direction of the fluid, towards the at least one flow orifice, to regulate a fluid flow through the at least one flow orifice,
wherein each of the at least one flow orifice is formed between two stationary flow restriction posts extending into the fluid flow channel spaced apart from one another,
wherein each stationary flow restriction post and a corresponding piston of the at least one piston defines a passage between one another, which passage has a cross-sectional extension which is dependent on a position of the corresponding piston relative to each of the stationary flow restriction posts, whereby the fluid flow through the passage is regulated by moving the corresponding piston towards the at least one flow orifice formed by the stationary flow restriction posts.

31. The micromachined fluid flow regulating device according to claim 30 wherein the stationary flow restriction posts and/or the corresponding piston are formed such that the passage varies in a linear or non-linear way while moving the corresponding piston towards the at least one flow orifice formed by the stationary flow restriction posts.

* * * * *